(12) United States Patent
Kowalczewski et al.

(10) Patent No.: US 7,837,599 B2
(45) Date of Patent: Nov. 23, 2010

(54) METHOD AND APPARATUS FOR AUTOMATED DELIVERY OF THERAPEUTIC EXERCISES OF THE UPPER EXTREMITY

(75) Inventors: Jan Kowalczewski, Edmonton (CA); Arthur Prochazka, Edmonton (CA)

(73) Assignee: Rehabtronics Inc., Edmonton, Alberta (CA)

( * ) Notice: Subject to any disclaimer, the term of this patent is extended or adjusted under 35 U.S.C. 154(b) by 455 days.

(21) Appl. No.: 11/747,771

(22) Filed: May 11, 2007

(65) Prior Publication Data

US 2007/0265146 A1 Nov. 15, 2007

Related U.S. Application Data

(60) Provisional application No. 60/747,084, filed on May 11, 2006.

(51) Int. Cl.
*A63B 23/12* (2006.01)
(52) U.S. Cl. ............... 482/44; 482/8; 482/46; 482/49; 482/139; 482/904
(58) Field of Classification Search ............ 482/44–46, 482/49, 51, 92, 97, 117, 138, 904, 8, 139; 434/247, 258–260; 601/40; 600/587, 595
See application file for complete search history.

(56) References Cited

U.S. PATENT DOCUMENTS 2,921,791 A 1/1960 Berne (Continued)

FOREIGN PATENT DOCUMENTS

FR 2585958 A1 * 2/1987

(Continued)

OTHER PUBLICATIONS

American Heart Association (2006) "Heart Disease and Stroke Statistics," 2006 Update, Dallas, Texas, p. e103.

(Continued)

*Primary Examiner*—Loan Thanh
*Assistant Examiner*—Victor K Hwang
(74) *Attorney, Agent, or Firm*—Greenlee Sullivan P.C.

(57) ABSTRACT

The invention provides a method and apparatus to enable a user to perform upper extremity exercises. The apparatus includes an arm with one end connected to a base to securely support the arm while locating the other end adjacent to the user, proximate the user's upper extremities. The arm is formed with a plurality of joints at or between its ends, each joint having one or more rotational degrees of freedom while providing resistance to rotational movement in the one or more degrees of freedom, such that the free end of the arm can be moved in three dimensional space, and such that the arm is self-supporting. A manipulandum assembly including a plurality of manipulanda is attached to the free end of the arm, each manipulandum being positioned within hand grasping range of the user, and each manipulandum being or representing an object encountered in an upper extremity activity of the user's daily life. Sensors on the arm, joints or manipulanda sense movement or force, and relay signals to a processing device in order to sample, display, store and process the signals into kinematic or kinetic variables. These variables may be processed to control software programs such as computer games and to allow quantification of performance for outcome evaluation of therapy regimes.

49 Claims, 11 Drawing Sheets

U.S. PATENT DOCUMENTS

| | | | | | |
|---|---|---|---|---|---|
| 3,239,184 | A | * | 3/1966 | Kirkeby | 248/568 |
| 4,235,437 | A | * | 11/1980 | Ruis et al. | 482/5 |
| 4,471,957 | A | | 9/1984 | Engalitcheff, Jr. | |
| 4,585,363 | A | * | 4/1986 | McGuire | 401/6 |
| 4,629,185 | A | * | 12/1986 | Amann | 482/113 |
| 4,872,668 | A | * | 10/1989 | McGillis et al. | 482/113 |
| 5,186,695 | A | * | 2/1993 | Mangseth et al. | 482/6 |
| 5,193,963 | A | | 3/1993 | McAffee et al. | |
| 5,466,213 | A | | 11/1995 | Hogan et al. | |
| 5,746,704 | A | | 5/1998 | Schenck et al. | |
| 5,755,645 | A | | 5/1998 | Miller et al. | |
| 6,007,459 | A | | 12/1999 | Burgess | |
| 6,186,961 | B1 | * | 2/2001 | Hanoun | 600/587 |
| 6,366,273 | B1 | * | 4/2002 | Rosenberg et al. | 345/156 |
| 6,477,448 | B1 | | 11/2002 | Maruyama | |
| 6,587,750 | B2 | * | 7/2003 | Gerbi et al. | 700/245 |
| 6,613,000 | B1 | | 9/2003 | Reinkensmeyer et al. | |
| 6,676,570 | B2 | * | 1/2004 | Valentino | 482/45 |
| 6,876,883 | B2 | * | 4/2005 | Hurtado | 607/48 |
| 6,961,623 | B2 | | 11/2005 | Prochazka | |
| 6,985,133 | B1 | * | 1/2006 | Rodomista et al. | 345/156 |
| 6,988,977 | B2 | | 1/2006 | Webber et al. | |
| 7,575,536 | B1 | * | 8/2009 | Hickman | 482/8 |
| 7,604,576 | B2 | * | 10/2009 | Drechsler | 482/99 |
| 2002/0094913 | A1 | | 7/2002 | Valentino | |
| 2005/0128186 | A1 | | 6/2005 | Shahoian et al. | |
| 2006/0094570 | A1 | * | 5/2006 | Schneider | 482/92 |

FOREIGN PATENT DOCUMENTS

| | | |
|---|---|---|
| WO | WO 98/19222 | 5/1998 |
| WO | WO 2004/034937 | 10/2003 |
| WO | WO 2005/074371 | 8/2005 |
| WO | PCT/CA2007/000828 | 11/2007 |

OTHER PUBLICATIONS

Dickstein et al. (1986) "Stroke Rehabilitation. Three exercise Therapy Approaches," *Phys. Ther.* 66:1233-1238.

Gritsenko et al. (2001) "Automated FES-Assisted Exercise Therapy for Hemiplegic Hand Function," *Soc. Neurosci. Abst.* 27:210-220.

Gritsenko et al. (2004) "A Functional Electric Stimulation-Assisted Exercise Therapy System for Hemiplegic Hand Function," *Arch. Phys. Med. Rehab.* 85:881-885.

Lai et al. (2002) "Persisting Consequences of Stroke Measured by the Stroke Impact Scale," *Stroke* 33:1840-1844.

Lum et al. (2006) "A Telerehabilitation Approach to Delivery of Constraint-Induced Movement Therapy," *J. Rehabil. Res. Dev.* 43:391-399.

Taub et al. (1999) "Constraint-Induced Movement Therapy: A New Family of Techniques with Broad Application to Physical Rehabilitation—A Clinical Review," *J. Rehab. Res. Dev.* 36:237-251.

Taub et al. (2005) "AutoCITE: Automated Delivery of CI Therapy with Reduced Effort by Therapists," *Stroke* 36:1301-1304.

International Search Report corresponding to International Application No. PCT/CA2007/000828, Mailed Aug. 20, 2007.

Written Opinion of the International Search Authority Corresponding to International Application No. PCT/CA2007/000828, Mailed Aug. 20, 2007.

European Search Report, Corresponding to European Application No. EP 07 71 9752, Completed Aug. 18, 2009.

International Preliminary Report on Patentability, Corresponding to International Application No. PCT/CA07/00828, Issued Nov. 11, 2008.

Written Opinion of the International Searching Authority, Corresponding to International Application No. PCT/CA07/00828, Mailed Aug. 20, 2007.

* cited by examiner

METHOD AND APPARATUS FOR AUTOMATED DELIVERY OF THERAPEUTIC EXERCISES OF THE UPPER EXTREMITY

CROSS-REFERENCE TO RELATED APPLICATION

This application claims the benefit under 35 USC §119 of U.S. Patent Application No. 60/747,084, filed May 11, 2006, the disclosure of which is incorporated herein by reference in its entirety to the extent not inconsistent herewith.

FIELD OF THE INVENTION

The present invention relates to a method and apparatus for rehabilitation, specifically in relation to physical therapy applied to the upper extremity.

BACKGROUND OF THE INVENTION

Impaired movement of the upper extremities often accompanies neuromuscular disorders such as stroke, spinal cord injury, multiple sclerosis, peripheral nerve damage and arthritis. The motor deficits result in a loss of independence, reduced quality of life and high costs of care. Stroke is the leading cause of upper extremity dysfunction. In developed countries, about 1.5% of the population live with the after-effects of stroke or about 5.5 million people in North America (American Heart Association, 2006). Functional recovery of the upper extremity after stroke is quite poor, with 55% to 75% of patients having significant permanent deficits in performing activities of daily life (Lai et al., 2002).

The most widely used rehabilitative techniques are Neuro-Developmental Treatment and Proprioceptive Neuromuscular Facilitation. Both are forms of exercise therapy which have been shown to be effective if performed on a regular basis over weeks or months (Dickstein et al., 1986). Another technique, Constraint Induced Therapy, was recently developed specifically for the rehabilitation of upper extremity function and involves intensive exercise therapy of the affected arm and hand, typically six hours per day for two weeks (Taub et al., 1999). Constraint Induced Therapy has been widely adopted around the world since large gains in function of the hemiplegic extremity in activities of daily life are achieved after two weeks.

However, the above techniques are time-consuming for therapists in that such techniques require one-on-one supervision, ideally on a daily basis. Furthermore, the types of exercises involved tend to vary from one treatment facility to another. Reimbursement is usually limited to the time patients are in a rehabilitation hospital. Following a hospital stay, patients are required not only to travel to physical therapy clinics, but also to absorb the costs of such services themselves. Such disadvantages prevent the large majority of potential beneficiaries of exercise therapy from receiving it.

Those skilled in the art have attempted to provide methods and devices suitable for machine delivery of exercise. For example, U.S. Pat. No. 6,007,459 to Burgess describes the use of an interactive video communications link which allows a therapist to supervise exercises performed by subjects located elsewhere, for example in their homes.

Another approach is to provide a subject with an interactive robotic system attached to the subject's limb. For example, U.S. Pat. No. 5,466,213 to Hogan et al. describes a robot which guides the limb along desired movement paths comprising a series of upper extremity exercises. The subject's robot can also be controlled remotely by a physical therapist using a second identical robot. The system can include a teleconferencing system allowing subject and therapist to communicate with each other. However, this technology is highly expensive, precluding it from widespread usage.

Other devices that impose movements on the hand have been suggested. For example, U.S. Pat. No. 5,746,704 to Schenck et al. teaches a motorized exercise device for imposing movements along a specified path on a digit of the hand. Such passive motion devices are problematic, either in being limited to particular anatomical parts such as a single digit, or not enabling active exercise of a representative range of upper extremity movements required for activities of daily life.

U.S. Pat. No. 5,755,645 to Miller et al. teaches a multiple degree of freedom passive exercise device in the form of a joystick with a telescopic arm, whereby the user grasps a handle and moves it in a three-dimensional workspace. Computerized control of two or more brakes creates programmable mechanical resistances within the workspace. This device allows the performance of many types of movement such as throwing a ball or swinging a baseball bat. Handle attachments including tennis rackets, golf clubs and hockey sticks are described. However, the complexities of the mechanism, controllers and software place this device into a price category unaffordable for widespread distribution into peoples' homes. U.S. Pat. No. 6,988,977 to Webber et al. describes a passive exercise device with a multi-jointed arm. This device is intended as part of a weight-lifting machine for upper body training. Both Miller et al. and Webber et al. describe manipulanda in the form of handles which are easily grasped; yet, such manipulanda are not even representative of the differently sized and shaped objects encountered in activities of daily life and which are most problematic for people with impaired hand function.

Exercise workstations have been designed with instrumented objects of different sizes and shapes and sensors attached to the objects to provide kinematic data to a computer. Gritsenko et al. (2001) describes a workstation in the form of a desk surface, with fixed objects such as a spring-loaded doorknob, a spring-loaded caliper, a weighted handle and loose objects such as blocks and cylinders. Gritsenko and Prochazka (2004) describes a workstation in the form of a circular table with a rotatable upper surface, bearing a similar range of fixed and loose objects. Taub et al. (2005) describes a cabinet with eight sets of fixed and loose objects arrayed on four work surfaces, each of which may be selected and manually pulled toward the subject from the cabinet. All of the described workstations are difficult to adjust, mechanically complex, bulky and expensive, rendering them undesirable for widespread usage in peoples' homes.

U.S. Pat. No. 6,613,000 to Reinkensmeyer et al. describes a more affordable passive exercise device. A mass-produced computer input device such as a joystick intended for computer games is used by the subject to perform hand movements. Signals from the joystick sensors are used to provide input to a computer that communicates to a server computer through a computer network. The server computer downloads individualized information to the subject's computer, specifying desired therapy and assessment exercises. The therapy and assessment exercises can be performed autonomously without real-time supervision from a therapist. The drawback of the device is that the range of movements performed by the subject is limited to the motion of the top of the joystick, namely a curved surface. The joystick knob is relatively easy to grasp, unlike many objects encountered in activities of daily life.

There is clearly a need for an inexpensive, straightforward device which addresses significant daily tasks such as grasping, lifting, lowering, moving side-to-side, twisting and otherwise manipulating objects of different sizes and shapes.

SUMMARY OF THE INVENTION

The present invention provides a method and apparatus for a range of movement exercises representative of activities of daily life. Significantly, the invention can incorporate various exercise tasks considered important by physical therapists. The invention can provide quantified measures of performance suitable for computerized patient records. Advantageously, the invention is simple and affordable, such that the health care system may be able to acquire and distribute it to the large numbers of people requiring sustained exercise therapy to improve upper extremity function.

In a broad aspect, the invention provides a method for performing upper extremity exercises by providing one or more manipulanda connected to a multi-jointed, self-supporting arm, the one or more manipulanda capable of being manipulated by a user to simulate movements representative of activities of the user's daily life.

In another broad aspect, the invention provides an apparatus to enable a user to perform upper extremity exercises, the apparatus comprising:

an arm having a fixed end and a free end, the fixed end being connected to a base for securely supporting the arm and to locate the free end adjacent to the user, proximate to the user's upper extremities;

a plurality of joints formed in the arm at or between its fixed and free ends, each joint having one or more rotational degrees of freedom while providing resistance to rotational movement in the one or more degrees of freedom, such that the free end of the arm can be moved in three dimensional space, and such that the arm is self-supporting; and a manipulandum assembly comprising a plurality of manipulanda attached to the free end of the arm in a manner such that each manipulandum can be moved by the user through the one or more rotational degrees of freedom provided by the plurality of joints, each manipulandum being positioned within hand grasping range of the user, and each manipulandum being or representing an object encountered in an upper extremity activity of the user's daily life.

In a preferred embodiment, the plurality of manipulanda are fixed or tethered to the free end of the arm such that the manipulanda so connected remain accessible to the user without dropping or becoming lost.

In another preferred embodiment, one or more of the manipulanda are attached to the free end of the arm such that an additional rotational degree of freedom is provided to the manipulanda so attached.

In another preferred embodiment, one or more of the manipulanda are mounted on a rotatable shaft connected at the free end of the arm such that the additional rotational degree of freedom is provided along the long axis of the shaft.

In another preferred embodiment, the plurality of joints provides passive resistance against rotational movement, and thereby returns the arm and the manipulandum assembly to an equilibrium rest position when the user releases the manipulandum assembly.

In yet another preferred embodiment the arm is positioned above a floor, and wherein the arm is formed in two interconnected segments with a first segment extending generally upwardly from the base and a second segment extending generally forwardly toward the user to position the free end proximate the user's upper extremities, the first segment having the fixed end connected to the base through a first joint providing a rotational degree of freedom in a horizontal axis generally parallel to the floor, and a rotational degree of freedom in a vertical axis, the first and second segments being interconnected through a second joint providing a rotational degree of freedom in a horizontal axis, and the free end of the second segment being attached to the plurality of manipulanda through a third joint providing a rotational degree of freedom in a horizontal axis.

Preferred and exemplary manipulanda of the present invention are selected from a vertically split cylinder, a doorknob manipulandum, a key-grip manipulandum, horizontal handles manipulandum, a peg manipulandum and a coin manipulandum.

In a further preferred embodiment the apparatus includes one or more sensors located in one or more positions selected from the first, second and third joints, the first and second segments, and the plurality of manipulanda, the sensors being operative to detect movement or force and to generate an electrical signal representative of movement or force generated.

In another broad aspect, the invention extends to a method for providing an exercising therapy for the user's upper extremity comprising providing an apparatus as described above, and causing the user to manipulate the plurality of manipulanda with the user's hand to simulate movements representative of activities of the user's daily life. Preferred forms of manipulating include grasping, squeezing, releasing, pinching, lifting, lowering, moving from side to side, twisting and rotating.

BRIEF DESCRIPTION OF THE DRAWINGS

The present invention will be further described by way of example only and with reference to the following figures in which similar references are used in different figures to denote similar components, and wherein:

FIG. 3A is a perspective view of the doorknob manipulandum positioned towards the user. FIG. 3B is a perspective view of the doorknob manipulandum in a rotated, upright position.

BRIEF DESCRIPTION OF THE PREFERRED EMBODIMENTS

The invention broadly provides a method and apparatus for physical therapy for various disorders in which movement of the upper extremity is impaired. The apparatus has a multi-jointed, self-supporting arm, the joints of which provide resistance (preferably passive resistance) to rotational movement in one or more degrees of freedom. One end of the arm, a connected end, is connected to a support for securely supporting the arm and for positioning the arm at an appropriate user height. The other end of the arm, the free end bears one or more manipulanda simulating movements representative of activities of the user's daily life. The design of the arm allows movement to any point within the biomechanical workspace of the user's hand. Each manipulandum in the assembly is designed to provide a specific hand and/or arm exercise involving certain movements representative of those occurring in an activity of daily life. The specific exercise provided by each manipulandum is similar to those used in conventional physical therapy for subjects with impaired movement of the upper extremities resulting from neuromuscular disorders. Such disorders can include, for example, stroke, spinal cord injury, multiple sclerosis, peripheral nerve damage and arthritis.

The following description is a preferred embodiment of the invention by way of example only and without limitation to the combination of features necessary for carrying out the invention into effect.

The invention is described with reference to the drawings in which like parts are labeled with the same numbers in FIGS. 1 to 8. The apparatus is shown generally at 10 in FIG. 1 to include a multi-jointed arm 12 with a connected manipulandum assembly 14 and computer 16.

Figure 1:
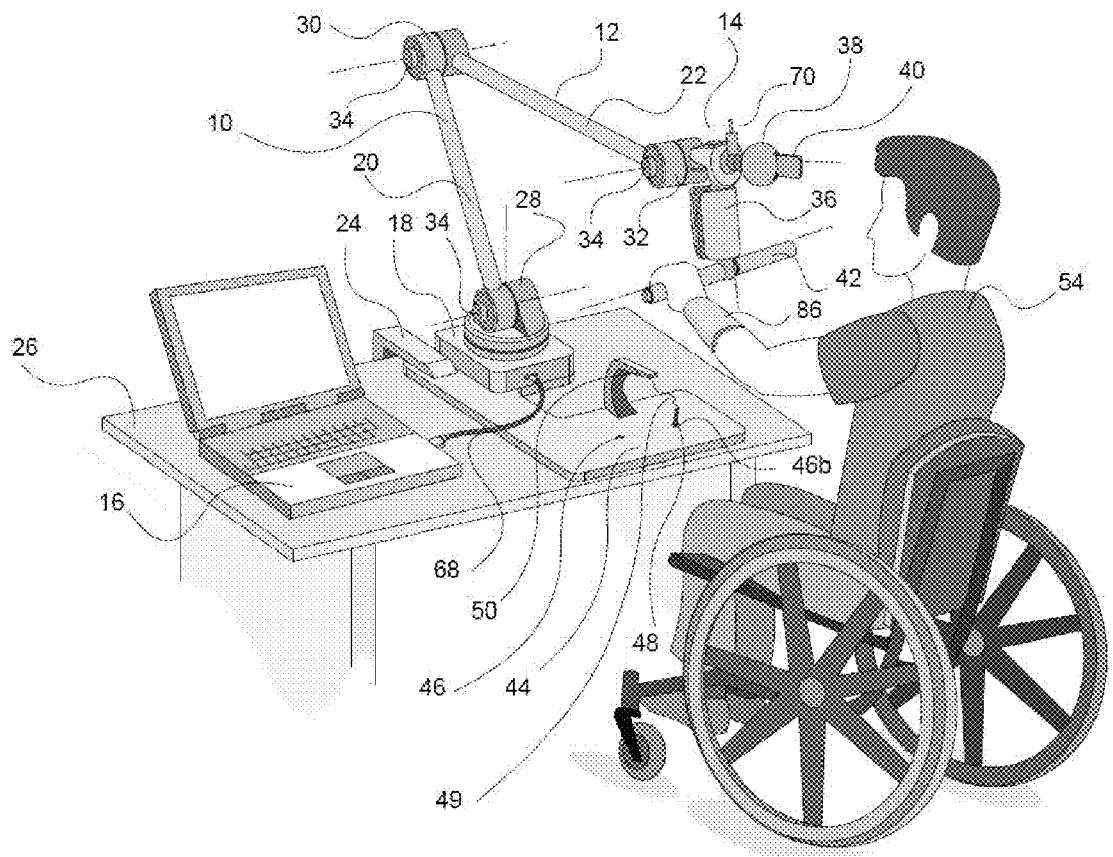
FIG. 1 is a perspective view of one embodiment of the present invention, showing the multi-jointed arm providing multiple rotational degrees of freedom to the plurality of manipulanda attached to the free end of the arm.

The arm 12 is composed of a base assembly 18, a first segment 20 and a second segment 22. The base assembly 18 is securely anchored by appropriate securing means, for example a clamp 24, to a horizontal support 26, for example, a desk, table or other suitable support. The base assembly 18 is connected to the fixed end of the first segment 20 by a first spring-loaded joint 28, preferably having two rotational degrees of freedom (as indicated by dashed lines in FIG. 1—showing rotational movement about a horizontal and a vertical axis). The first segment 20 is linked to the second segment 22 by a second spring-loaded joint 30, preferably having a single rotational degree of freedom (as indicated by the dashed line in FIG. 1—showing rotation about a horizontal axis). The manipulandum assembly 14 is connected to the free end of the second segment 22 by a third spring-loaded joint 32, preferably having a single rotational degree of freedom (as indicated by the dashed line in FIG. 1—showing rotation about a horizontal axis). In FIG. 1, the free end of the arm 12 (or segment 22) terminates at the third joint 32.

The first and second segments 20, 22 can be formed of a rigid material. Alternatively, telescopic, elastic, or rotational segments can be used to provide additional degrees of freedom beyond those of the rigid segments 20, 22 illustrated in FIG. 1. Such segments may be instrumented to measure deflection, extension, compression and rotation.

Each of the spring-loaded joints 28, 30, 32 can be locked in a certain position using any known locking means (not shown) within its respective range of motion if so desired. One example of suitable locking means is a bolt and wing nut. Each spring-loaded joint 28, 30, 32 provides passive resistance to angular deflection away from a static equilibrium position (equilibrium rest position) determined by the mass and spring properties of the components of the apparatus 10.

In this manner, the multi-jointed arm 12 is self-supporting, and will return to its equilibrium rest position when the user completes a particular manipulation, releasing a manipulandum. Springs are incorporated in the joints 28, 30, 32 to achieve a desired amount of passive resistance in movement. Alternatively, a desired amount of resistance is achieved using friction bearings, dampers or weights, although springs are preferable. It is understood that these means of resistance may be varied, thus allowing for alterations in manipulanda, user and user capabilites. Each spring-loaded joint 28, 30, 32 in the arm 12 is preferably equipped with a sensor 34 for electrically measuring its angle of deflection around its respective rotational axis or axes.

The exemplary embodiment incorporates spring-loaded joints 28, 30, 32. It is possible to modify the invention to incorporate other suitable types of joints, for example, joints having additional rotational degrees of freedom, differing or absent spring-loading, differing or absent locking means, and different instrumentation. For instance, a ball and socket joint can be used to connect the first and second segments 20, 22. The ball and socket joint may be spring-loaded, or may rely on friction to maintain a position. Advantageously, the ball and socket joint has rotational degrees of freedom around two axes, and can be instrumented with sensors 34 that measure deflection of the joint around its two degrees of freedom.

In general, any joints or linkages which provide one or more rotational degrees of freedom with some resistance to rotational movement are suitable. Most preferably, the joints provide only passive resistive force against rotational movement, such as by frictional, spring, gravitational, or inertial force. It should be understood that the provision of passive resistance to rotational movement in the joints is meant to exclude the use of force generators or robotic devices.

One or more moving components of the apparatus 10 (for example, arm, segments, joints, manipulanda, and pegboard holes) are instrumented with electronic sensors 34 (see also sensors 74, 84 described below with particular manipulanda). The sensors 34 detect the movement of one or more moving components and generate electrical signals representative of the movement. The electrical signals are then transmitted to a suitable processing device, such as the computer 16, which then samples, displays, stores and processes the signals into kinematic or kinetic variables. Secondary variables such as, for example, net displacement, velocity, acceleration, force and torque, are computed from the kinematic or kinetic variables to generate performance ratings or scores. It has been found advantageous to compute a single performance rating by first normalizing each individual rating corresponding to a given exercise and combining all such ratings into a single score (see for example, Gritsenko & Prochazka, 2004).

Various types of sensors 34 are appropriate with the apparatus 10. The exemplary embodiment uses potentiometers to determine the angle of a joint or the position of the first and second segments 20, 22. Other non-limiting examples include potentiometers, gyroscopes, accelerometers, linear variable displacement transducers, optical encoders, strain gauges, electrical contacts, photo-electric sensors or other sensors known to those skilled in the art. Optical, electro-optical, magnetic, capacitive, inductive or other types of sensors can be used to quantify movement, position, orientation, or force applied to all or any combination of joints, segments, and manipulanda. In this manner, movement sensors located on one or more of the arm 12, segments 20, 22, joints 28, 30, 32 and manipulandum assembly 14 can be used to detect and transmit information from which one may calculate angles, starting and end point positions of components so as to generate information relating to the x, y and z co-ordinates of one or more of the manipulanda being moved by the user 54.

Figure 3A:
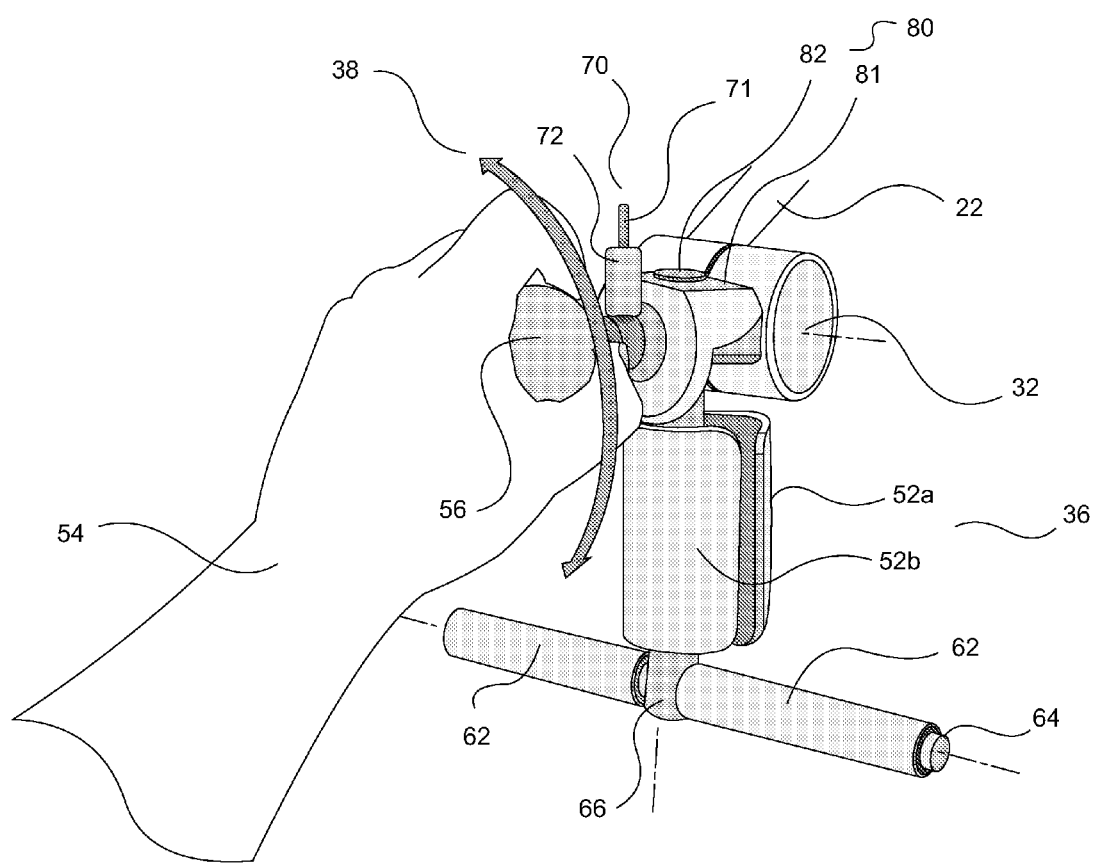
FIGS. 3A and 3B are perspective views of the doorknob manipulandum of one embodiment of the invention.
Figure 3B:
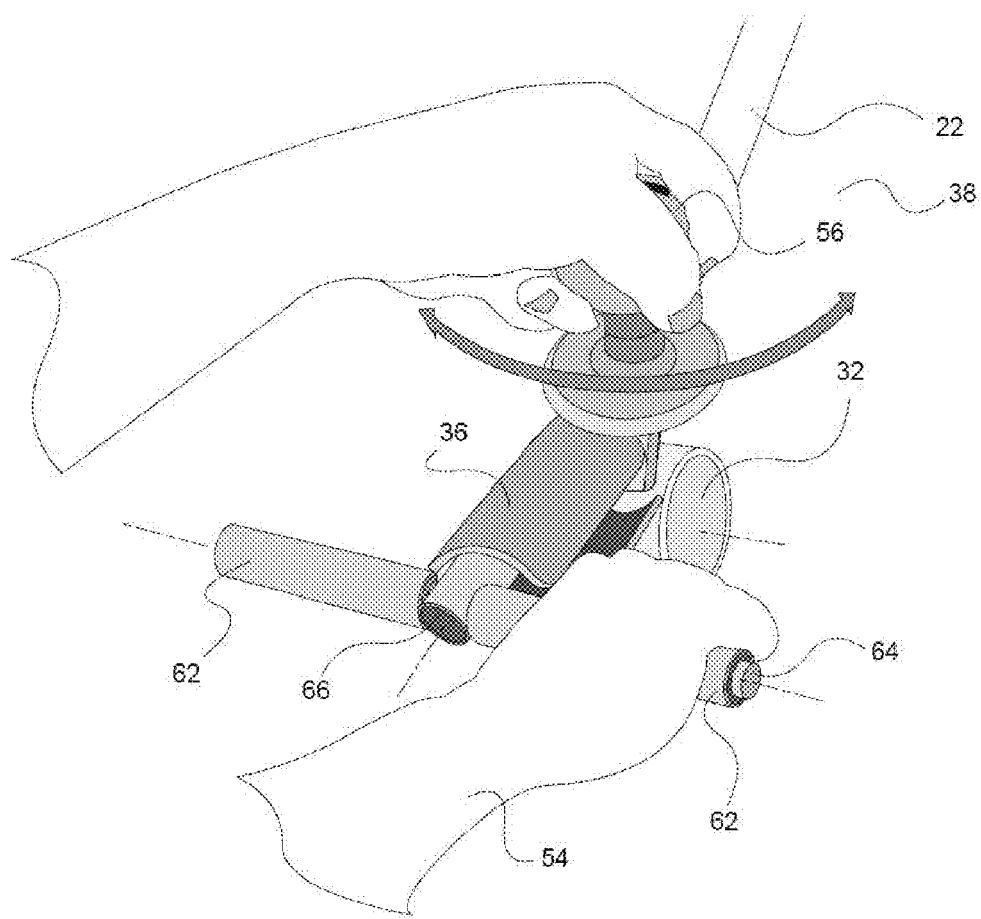

The manipulandum assembly 14 is connected to the free end of the second segment 22 through the joint 32. The manipulandum assembly preferably includes a platform 81 which extends forwardly from (i.e., toward the user), and is connected to, the joint 32. In this manner, the manipulandum assembly 14 can suspend a plurality of hand function manipulanda in front of the user, allowing the user to grasp each manipulandum with one or both hands, and move the manipulandum through the multiple degrees of freedom allowed by the joints 28, 30, 32. The platform 81 can be positioned generally horizontally, as shown in FIG. 3A, or it can be moved to be generally vertical as shown in FIG. 3B, by rotating the joint 32 along its horizontal axis. The manipulandum assembly 14 preferably also includes a shaft 66 mounted perpendicularly to the platform 81 (preferably below, as shown in FIG. 3A). The shaft 66 is preferably connected to the platform 81 for rotation about its long axis (shown in FIG. 3A as a vertical dotted line representing a vertical axis when the manipulandum apparatus 14 is in its upright position). This allows for connection of manipulanda as described below to this rotatable shaft 66, adding an additional rotational degree of freedom to a manipulandum of the manipulandum assembly 14. As shown in FIG. 1, the user 54 can move the manipulandum assembly 14, relative to the user, forwardly or rearwardly, up and down, and in a twisting or side to side movement, with the twisting or side to side movement being achieved through the vertical axis through joint 28 and/or the long axis of the rotatable shaft 66. Locking of one or more of these joints 28, 30, 32 or the rotatable shaft 66 to limit any of these rotational degrees of freedom may be achieved with the locking means (not shown), as mentioned below. Thus, the multi-jointed arm 12 allows for 3-dimensional movement of the manipulandum assembly 14, which can be sensed to generate x, y, and z components of the movements of the individual manipulandum by the user.

Another preferred feature of the manipulandum assembly 14 is that it allows for the one or more manipulanda to be fixed or tethered at the free end of the arm 12. In this manner, the manipulanda remain accessible to the user, without individual components being dropped or lost by the user.

The manipulandum assembly 14 is comprised of an electrically instrumented set of manipulanda which are self-supporting and provide resistance. Movement of such manipulanda requires upper extremity movements similar to those occurring in activities of daily life. Varied manipulanda are attached or detached from the arm 12, depending on the user's disorder, requirements or maintenance needs. It will be appreciated by those skilled in the art that different manipulanda can be connected to the arm 12 at different locations and with differing and/or additional degrees of freedom (i.e., additional to the rotational degrees of freedom provided by the joints 28, 30 and 32). As described in more detail below, additional sensors (i.e., in addition to sensors 34 located on the arm 12, segments 20, 22 and/or joints 28, 30 and 32) are preferably included to measure displacements of different manipulanda within the manipulandum assembly 14, from which secondary variables (for example, kinematic variables) are computed.

Without being limiting in any manner, the manipulandum assembly 14 may include, for example, one or more of a vertically split cylinder manipulandum 36; a doorknob manipulandum 38; a key-grip manipulandum 40; a horizontal handles manipulandum 42; a peg manipulandum 70; a coin manipulandum 80, or other suitable hand function manipulanda as used in conventional physical therapy for users with impaired movement of the upper extremity. As described more fully below, these manipulanda are preferably attached to the platform 81, to rotate with the joint 32, and/or to the rotatable shaft 66.

Figure 6:
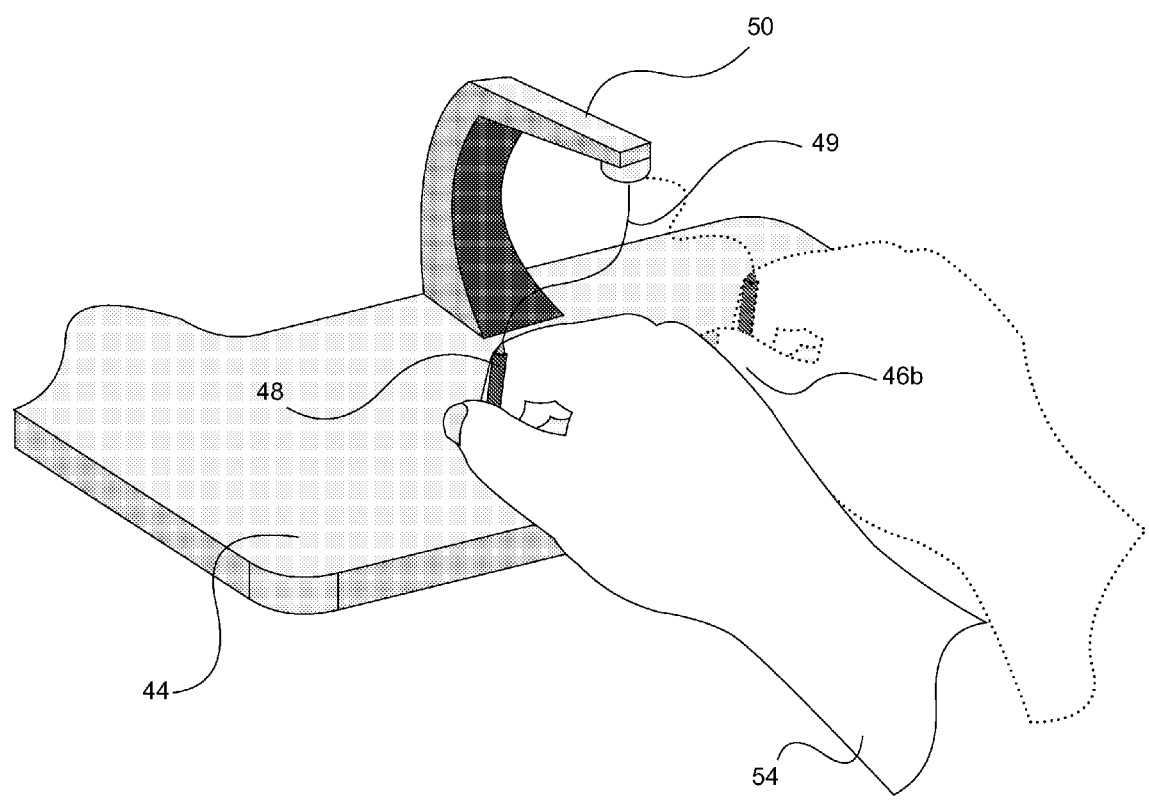
FIG. 6 is a perspective view of the pegboard and tethered peg manipulandum of one embodiment of the invention.

As shown in FIGS. 1 and 6, stationary manipulanda may be provided on a horizontal support 26 in front of the user. FIG. 6 shows one such exemplary additional manipulandum in the form of a pegboard 44 defining one or more holes 46 and having at least one peg 48 tethered by a tether 49 from a gantry 50 can be used alone or in combination with the apparatus 10.

Figure 2:
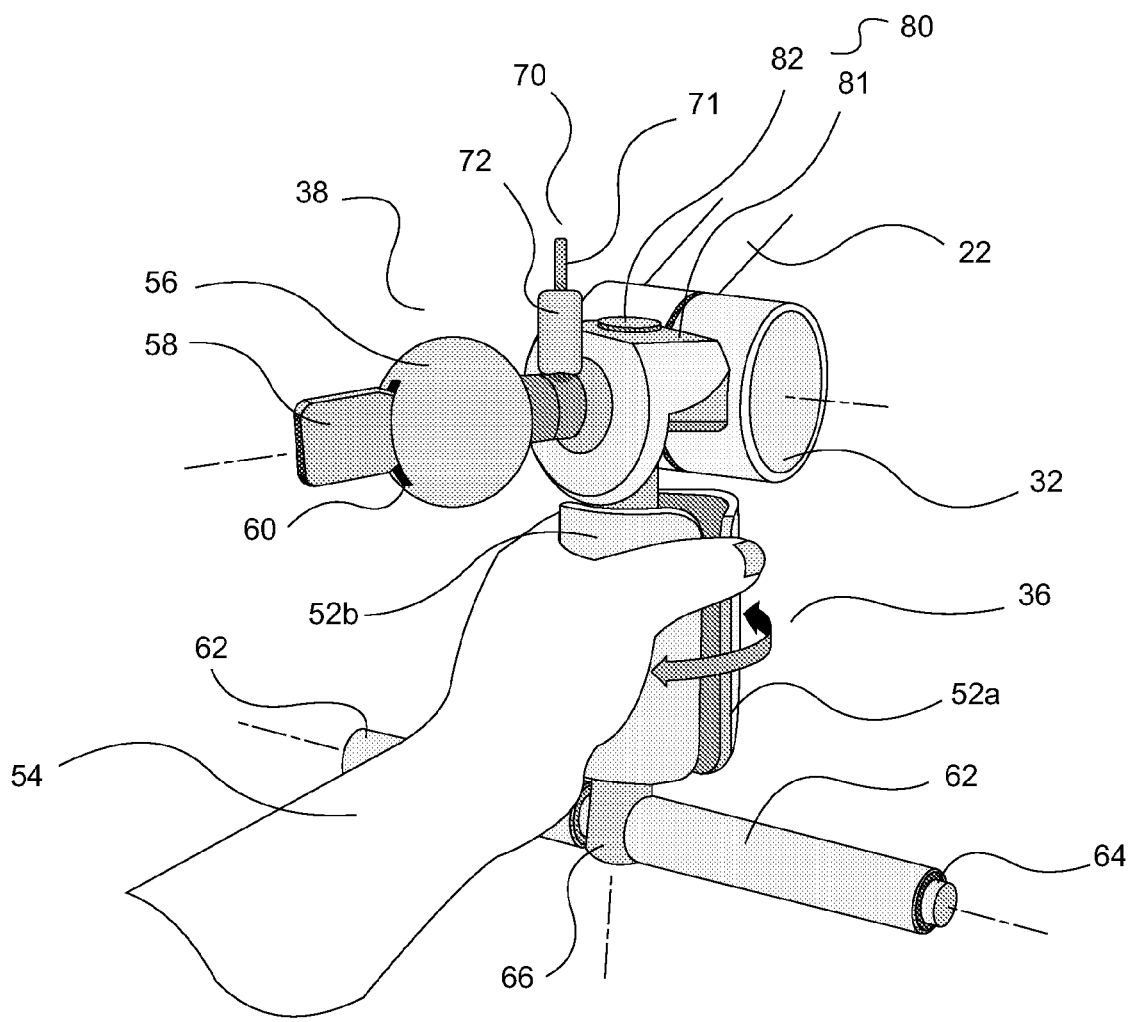
FIG. 2 is a perspective view of the split cylinder manipulandum of one embodiment of the present invention, showing the user grasping and squeezing manipulations on the split cylinder.

FIG. 2 shows the vertically split cylinder 36 defining two halves 52a, 52b mounted on the rotatable shaft 66, and which are biased slightly away from each other by one or more stiff springs (not shown). The split cylinder 36 doubles as a caliper for squeezing or a familiar object such as a pop can. Force may be sensed indirectly by displacement of the spring separating the two halves 52a, 52b of the split cylinder 36, or by a force transducer such as a strain gauge attached to part of the cylinder (sensor not shown). FIG. 2 illustrates the user 54 applying force to squeeze the two halves 52a, 52b of the split cylinder 36 together. The user 54 can also practice moving the split cylinder 36 from one position to another position within the workspace, mimicking the transfer of a familiar object such as a pop can from one location to another location.

FIGS. 3A and 3B show the doorknob manipulandum 38 comprising a rotatable spring-loaded doorknob 56 fixed for rotation to the platform 81. The doorknob 56 provides twisting (pronation-supination) exercises for the user 54, as shown in FIG. 3A. Conveniently, the doorknob 56 is rotatable into a vertical position, whereby the exercise requires a movement similar to that of twisting the lid of a screw-top jar, as shown in FIG. 3B. In other embodiments of the invention, the doorknob 56 can be replaced by different manipulanda. Non-limiting examples include a sphere, oval, lever or other shapes which simulate other activities of daily life.

Figure 4:
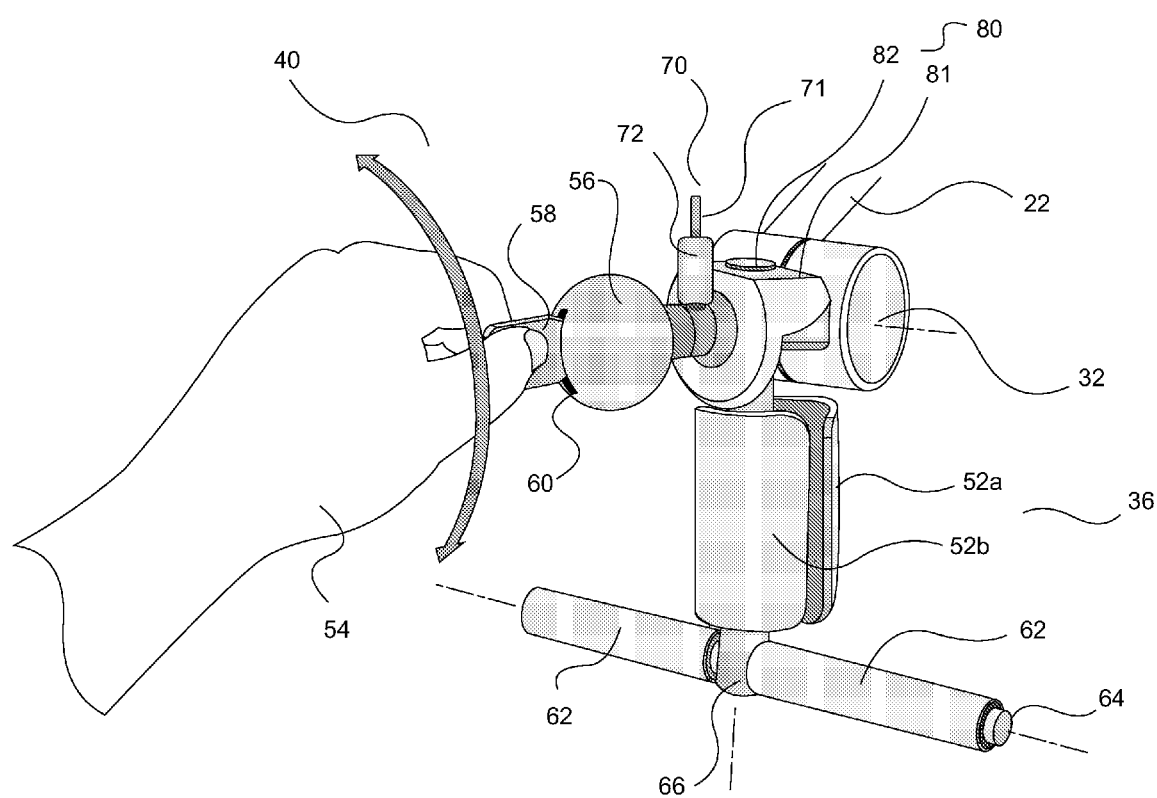
FIG. 4 is a perspective view of the key-grip manipulandum of one embodiment of the invention.

FIG. 4 shows a key-grip manipulandum 40 comprising a key-like tab 58 extending outwardly from a key way 60 defined in the doorknob 56. The key-like tab 58 is configured to be pulled outwardly from the key way 60 by the user 54 to a pre-configured locked position, so that the key-like tab 58 cannot be completely removed from or drop out of the key way 60. The key-like tab 58 can be twisted in a movement which mimics the turning of a key in a lock.

Figure 5:
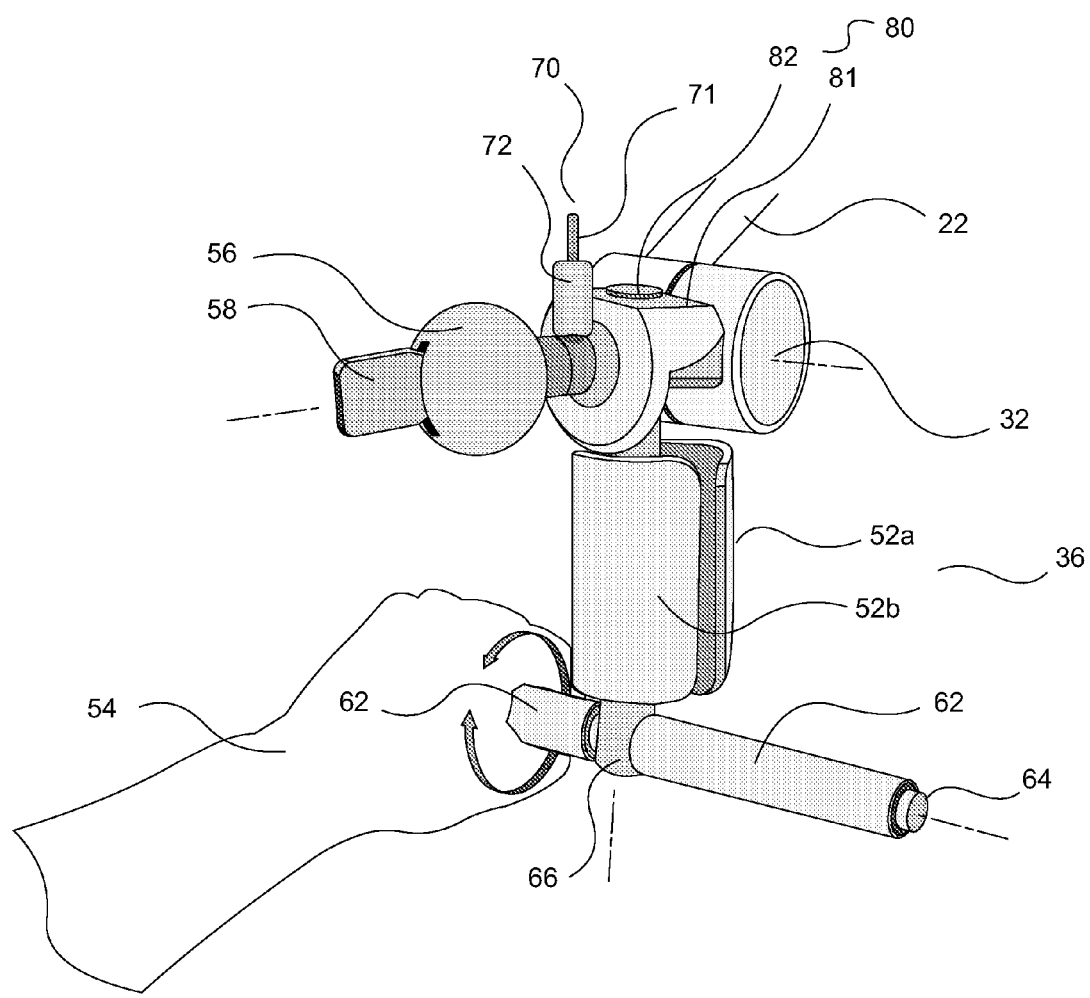
FIG. 5 is a perspective view of the horizontal handles manipulandum of one embodiment of the invention.

FIG. 5 shows the horizontal handles manipulandum 42 comprising horizontal handles 62 freely rotatable on an axle 64 which is secured to the base of the rotatable shaft 66, below the split cylinder 36. The handles 62 are positioned perpendicular to the split cylinder 36 (when in the equilibrium rest position) and extend horizontally beyond the periphery of the split cylinder 36 so as to be accessible to both the left and right hands of the user 54. The handles 62 rotate freely on the axle 64 which is connected to the manipulandum assembly 14, which, when combined with the degrees of freedom of the arm 12, allow any orientation of the user's hand 54 in the three-dimensional workspace. Advantageously, the handles 62 provide range-of-motion exercises encompassing virtually the entire biomechanical range of possible positions of the user's hand 54.

The exemplary embodiment can also be provided with a pegboard 44 attached to the horizontal support 26 as shown in FIG. 6. The pegboard 44 defines one or more holes 46, and has at least one peg 48 tethered by a tether 49 from a gantry 50. The pegboard 44 can be used alone or in combination with the apparatus 10. In use, the user 54 moves the peg 48 from a first hole 46a to a second or other hole 46b in order to practice side-to-side movement of the hand 54 (the movement of the hand 54 is shown in phantom in FIG. 6). Sensors 34 can be positioned within the one or more holes 46 to monitor or assess the user's progress.

Figure 7A:
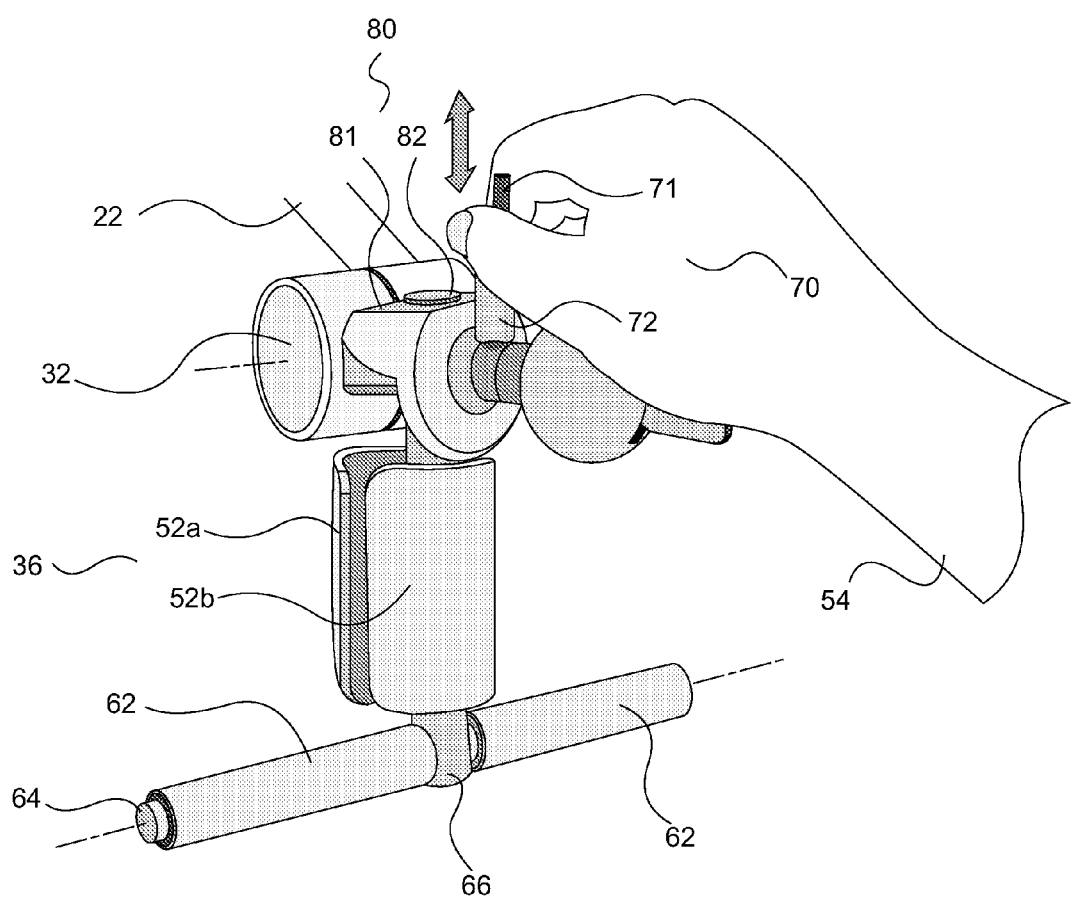
FIG. 7A is a perspective view of the peg manipulandum and the coin manipulandum of one embodiment of the invention.
Figure 7B:
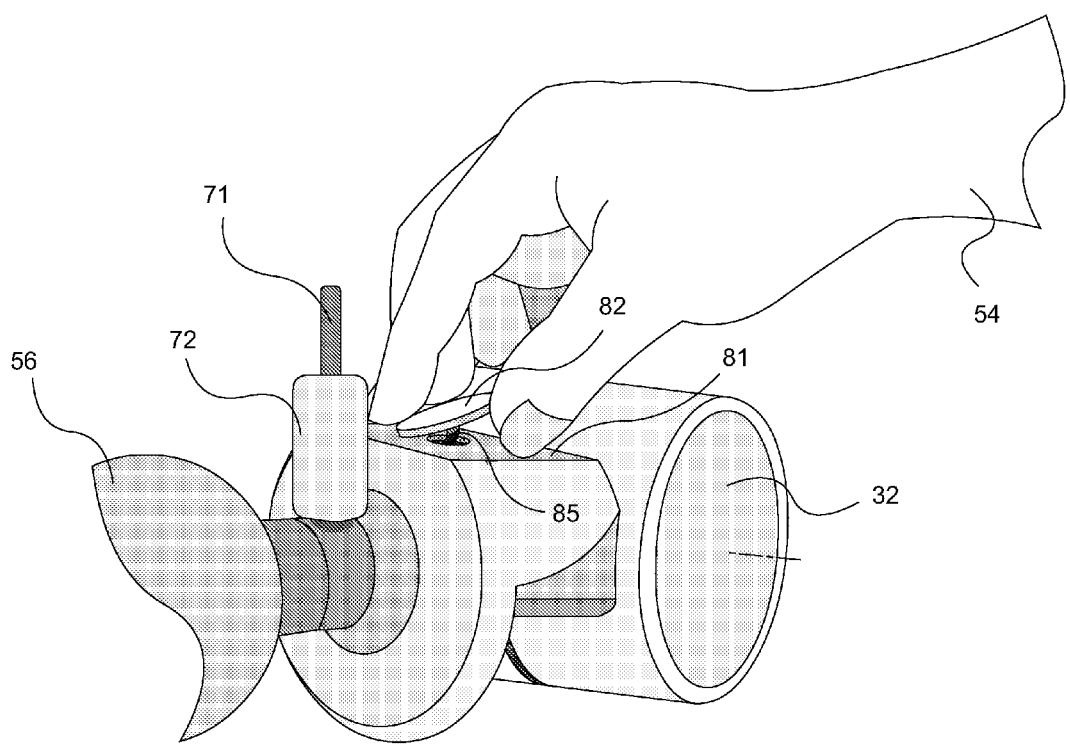
FIG. 7B is a perspective view of the peg and coin manipulandum of FIG. 7A, showing the peg and coin housing parts in cross section to show the spring loaded peg, tethered coin and sensor details.
Figure 7C:
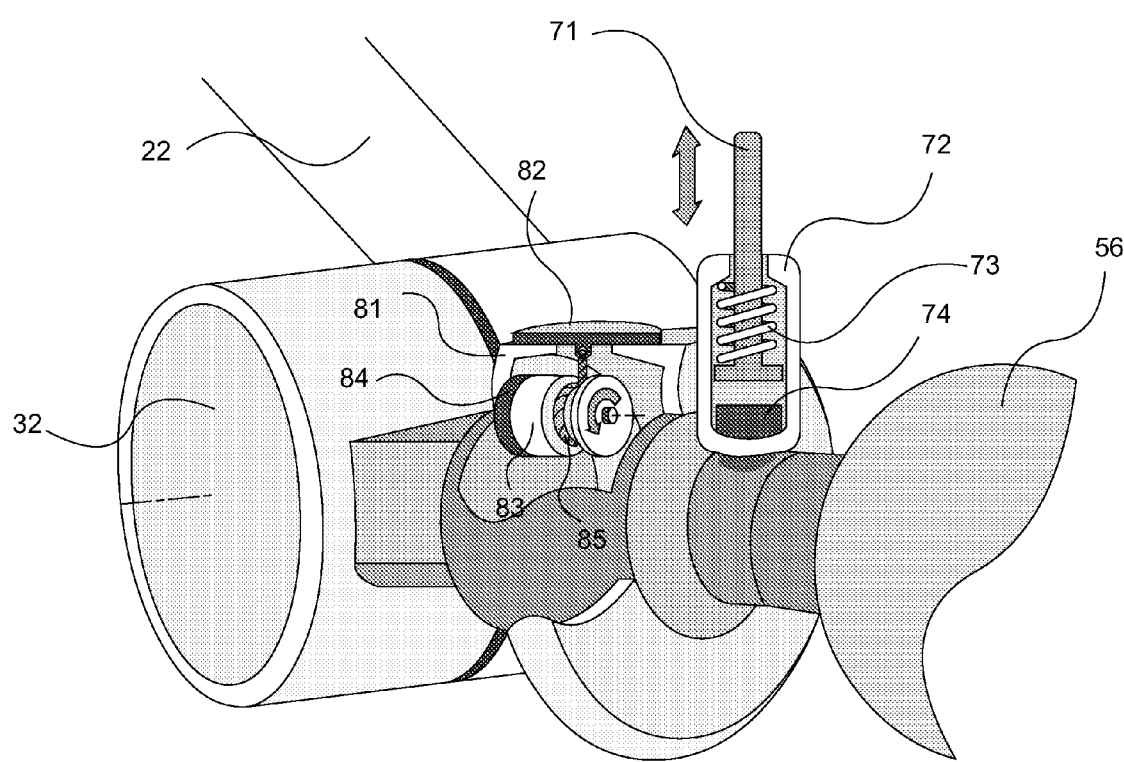
FIG. 7C is a perspective view of the coin manipulandum of FIG. 7A, showing the user manipulating the coin manipulandum in a manner to simulate picking up the coin element.

FIGS. 7A, 7B and 7C show exemplary embodiments of a peg manipulandum 70 and a coin manipulandum 80 also provided at the free end of the arm 12, preferably forward of the platform 81. A peg 71 with an enlarged base is held captive in a hollow housing 72. A spring 73 within the housing normally pushes the enlarged base of the peg 71 against a sensor 74 such as a microswitch located at the bottom of the housing 72. In use, the user 54 grasps the peg 71 in a pinch grip and pulls it part of the way out of the housing 72 against the resistance of the spring 73. This changes the state of the sensor 74. In addition to peg 71 being pulled partly out of the housing 72, it may also be moved in any direction in 3-dimensional space by virtue of its attachment to the moveable manipulandum assembly 14. The movement of the peg 71 and attached manipulandum assembly 14 may be computed from signals from the sensors 34.

The coin manipulandum 80 is shown to be mounted on the platform 81, although it might be mounted at an alternate convenient location on the manipulandum assembly 14 (it might still alternatively be mounted on the horizontal support 26, if desired). A coin element 82 is held flat on the platform 81. The coin element 82 may be tethered beneath the platform 81 in any suitable manner such that its removal from the platform 81 as the user picks up the coin element 82 may be sensed. FIG. 7B shows one exemplary embodiment in which the cross sectional details show a tether 85 connected to the underside of the coin element 82. The tether 85 is secured below the platform 81 to a self retracting spring biased reel 83. A motion sensor 84 may be mounted to the reel 83 in order to sense rotation of the reel 83 as the user 54 picks up the coin element 82.

While not specifically shown in the Figures, it will be understood by one skilled in the art that the apparatus and method of this invention may include one or more supporting devices for the user's hands or arms. Such supports might include, for example, elbow supports or overhead slings. As well, the invention might be adapted to use hand straps with one or more of the manipulanda in order to assist a user.

When the apparatus 10 is in use, the user 54 is generally seated and facing the manipulandum assembly 14, as shown in FIG. 1. The user 54 engages one of the manipulanda by grasping and lifting, lowering, pulling, pushing, twisting or otherwise moving it according to the activities of daily life being simulated, and according to a series of instructions provided by software in the computer 16, for example on the display or by a remote therapist communicating via a telecommunications link such as that mediated by the computer 16 through a network. The movements of the first, second and third spring-loaded joints 28, 30, 32 and first and second segments 20, 22 of the apparatus 10 are detected by the sensors 34. The sensors 34 in turn generate electrical signals representative of the movement, and transmit the electrical signals by suitable transmission means 68 (for example, a wire or wireless means) to a processing device such as the computer 16, which then samples, displays, stores and processes the signals into kinematic or kinetic variables. The kinematic or kinetic variables can be further processed to obtain secondary variables.

The computer 16 runs a software program that provides feedback and instruction to the user 54 based on the user's movements. The computer 16 also stores data captured by the sensors 34. The data may be processed subsequently to quantify changes in the user's ability to perform simulated activities of daily life over a period of time. A report of the user's progress may be periodically sent over a computer network to a computer located remotely for a therapist or trainer for analysis, for example through the Internet. The therapist or trainer can issue commands to the computer 16, locally or over a computer network, to modify or change the feedback and instruction the user 54 receives from the computer 16.

The computer interface can comprise different assemblies including, for example, both wired and wireless interfaces, for example USB and 802.11b, respectively. Computer programs of different types and levels of network and device connectivity can be used. Without being limiting in any manner, such types can include stand-alone applications, applications run from remote locations over a computer network, game applications, exercise applications and training applications. The computer program may offer many kinds of feedback to the user including audio and/or video. For instance, the computer program can allow an administrator either locally or by means of a computer network to communicate with the user in real time, or with a delay, by way of text, audio visual, or other type of communication.

Figure 8:
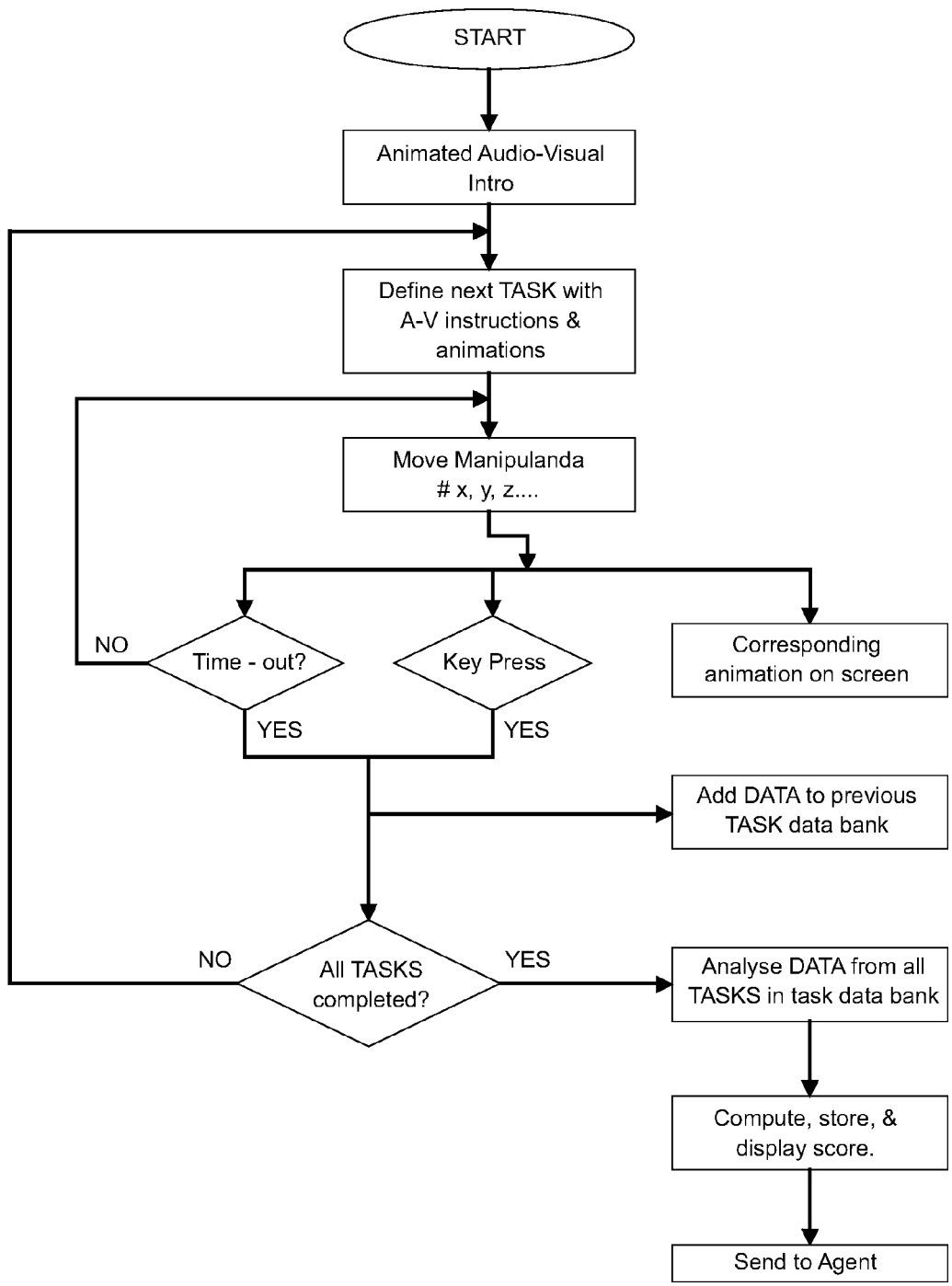
FIG. 8 is a flowchart illustrating one embodiment of computer software which might be used for interactive user prompting, scoring and transmitting to a remote location.

One example of computer software that can be used to guide the user 54 through a series of motor tasks that collectively comprise a standardized test of upper extremity function is shown in the flowchart of FIG. 8. Communication with the user 54 may be in the form of automatically generated voice commands, displayed text, pictures, videos and animations on the user's computer display 16. Alternatively or additionally, an administrator or therapist may provide verbal and visual guidance. As described above, the administrator may be in the same location or elsewhere, communicating verbally and visually by telecommunications means, for example with the use of the Internet. The software may record signals captured by the sensors 34 etc. during the performance of the standardized test and use these signals automatically to detect whether a specific task has or has not been attempted and prompt the user accordingly. The software may automatically compute performance scores from the captured data and thereby provide outcome measures from the standardized test.

The computer 16 can be a standalone workstation, or connected to a computer network. When connected to a network, the computer program can use a wide range of connectivity protocols over a link with the network. The computer 16 can be connected to multiple forms of networks simultaneously, for example a computer network and a cellular network.

The exemplary embodiment can be provided with an electrical stimulator 86 to activate the nerves and muscles of the user 54 to assist in the performance of the exercise (see for example, International Patent Application Publication No. WO 2004/034937 and U.S. Pat. No. 6,961,623 issued Nov. 1, 2005, both to Prochazka).

All references mentioned in this specification are indicative of the level of skill in the art of this invention. All references are herein incorporated by reference in their entirety to the same extent as if each reference was specifically and individually indicated to be incorporated by reference. However, if any inconsistency arises between a cited reference and the present disclosure, the present disclosure takes precedence. Some references provided herein are incorporated by reference herein to provide details concerning the state of the art prior to the filing of this application, other references may be cited to provide additional or alternative device elements, additional or alternative materials, additional or alternative methods of analysis or application of the invention.

The terms and expressions used are, unless otherwise defined herein, used as terms of description and not limitation. There is no intention, in using such terms and expressions, of excluding equivalents of the features illustrated and described, it being recognized that the scope of the invention is defined and limited only by the claims which follow. Although the description herein contains many specifics, these should not be construed as limiting the scope of the invention, but as merely providing illustrations of some of the embodiments of the invention. One of ordinary skill in the art will appreciate that elements and materials other than those specifically exemplified can be employed in the practice of the invention without resort to undue experimentation. All art-known functional equivalents, of any such elements and materials are intended to be included in this invention. The invention illustratively described herein suitably may be practiced in the absence of any element or elements, limitation or limitations which is not specifically disclosed herein.

As used herein, "comprising" is synonymous with "including," "containing," or "characterized by," and is inclusive or open-ended and does not exclude additional, unrecited elements. The use of the indefinite article "a" in the claims before an element means that one or more of the elements is specified, but does not specifically exclude others of the elements being present, unless the contrary clearly requires that there be one and only one of the elements.

REFERENCES

American Heart Association: Heart Disease and Stroke Statistics—2006 Update, Dallas, Tex. p. e103).

Dickstein, R.; Hocherman, S.; Pillar, T. and Shaham, R. (1986) Stroke rehabilitation. Three exercise therapy approaches. *Physical Therapy* 66:1233-8.

Gritsenko, et al. (2001) Automated FES-assisted exercise therapy for hemiplegic hand function. *Society for Neuroscience Abstracts* 27:210.220

Gritsenko, V. and Prochazka, A. (2004) A functional electric stimulation-assisted exercise therapy system for hemiplegic hand function. *Archives of Physical Medicine and Rehabilitation* 85:881-885.

Taub, E.; Lum, P. S.; Hardin, P.; Mark, V. W. and Uswatte, G. (2005) AutoCITE: automated delivery of CI therapy with reduced effort by therapists. *Stroke* 36:1301-1304.

Lai, S. M.; Studenski, S.; Duncan, P. W. and Perera, S. (2002) Persisting consequences of stroke measured by the Stroke Impact Scale. *Stroke* 33:1840-4.

Taub, E.; Uswatte, G. and Pidikiti, R. (1999) Constraint-induced Movement Therapy: a new family of techniques with broad application to physical rehabilitation—a clinical review. *Journal of Rehabilitation Research & Development* 36:237-251.

PATENT DOCUMENTS

Burgess, B. Method and system for providing physical therapy services. U.S. Pat. No. 6,007,459, issued Dec. 28, 1999.

Hogan, N.; Krebs, H. I.; Sharon, A.; and Charnnarong, J. Interactive robotic therapist. U.S. Pat. No. 5,466,213, issued Nov. 14, 1995.

Miller, L. C.; Ulrich, N.; Townsend, W. T.; Yoerger, D.; Matsuoka, Y.; and Larocque, B. D. Exercise apparatus. U.S. Pat. No. 5,755,645, issued May 26, 1998.

Prochazka, A. Method and apparatus for controlling a device or process with vibrations generated by tooth clicks. International Patent Application Publication No. WO 2004/034937, published Oct. 16, 2003.

Prochazka, A. Method and apparatus for controlling a device or process with vibrations generated by tooth clicks. U.S. Pat. No. 6,961,623, issued Nov. 1, 2005.

Reinkensmeyer, D. J.; Painter, C. C. and Pang, C. T. Method and apparatus for mass-delivered movement rehabilitation. U.S. Pat. No. 6,613,000, issued Sep. 2, 2003.

Schenck, R. R. and Krevald, W. R. Therapy apparatus having a passive motion device for flexing a body member. U.S. Pat. No. 5,746,704, issued May 5, 1998.

Webber, R. T. and Zink, G. M. Exercise arm assembly for exercise machine. U.S. Pat. No. 6,988,977, issued Jan. 24, 2006.

What is claimed is:

1. An apparatus to enable a user to perform upper extremity exercises, the apparatus comprising:
    an arm having a fixed end and a free end, the fixed end being connected to a base for securely supporting the arm and to locate the free end adjacent to the user, proximate to the user's upper extremities;
    a plurality of joints formed in the arm at or between its fixed and free ends, each joint having one or more rotational degrees of freedom while providing resistance to rotational movement in the one or more degrees of freedom, such that the free end of the arm can be moved in three dimensional space, and such that the arm is self-supporting; and
    a manipulandum assembly comprising a plurality of hand function manipulanda attached to the free end of the arm in a manner such that each manipulandum can be moved by the user through the one or more rotational degrees of freedom provided by the plurality of joints, each manipulandum being positioned within hand grasping range of the user, each manipulandum being configured to represent a different object encountered in an upper extremity activity, and the plurality of hand function manipulanda includes two or more of a vertically split cylinder manipulandum, a doorknob manipulandum, a key-grip manipulandum, a horizontal handles manipulandum, a peg manipulandum and a coin manipulandum.

2. The apparatus as set forth in claim 1, wherein the plurality of manipulanda is fixed or tethered to the free end of the arm such that the manipulanda so connected remain accessible to the user without dropping or becoming lost.

3. The apparatus as set forth in claim 2, wherein one or more of the manipulanda are attached to the free end of the arm such that an additional rotational degree of freedom is provided to the manipulanda so attached.

4. The apparatus as set forth in claim 3, wherein one or more of the manipulanda are mounted on a rotatable shaft connected at the free end of the arm such that the additional rotational degree of freedom is provided along the long axis of the shaft.

5. The apparatus as set forth in claim 4, wherein the plurality of joints provides passive resistance against rotational movement, such that the arm and the manipulandum assembly adopt an equilibrium rest position when not in use.

6. The apparatus of claim 5, wherein the arm is positioned above a floor, and wherein the arm is formed in two interconnected segments with a first segment extending generally upwardly from the base and a second segment extending generally forwardly toward the user to position the free end proximate the user's upper extremities, the first segment having the fixed end connected to the base through a first joint providing a rotational degree of freedom in a horizontal axis generally parallel to the floor, and a rotational degree of freedom in a vertical axis, the first and second segments being interconnected through a second joint providing a rotational degree of freedom in a horizontal axis, and the free end of the second segment being attached to the plurality of manipulanda through a third joint providing a rotational degree of freedom in a horizontal axis.

7. The apparatus of claim 6, wherein the first, second and third joints are spring-loaded joints with a spring in the joint or ball and socket joints.

8. The apparatus of claim 7, wherein the plurality of manipulanda includes two or more of a vertically split cylinder manipulandum, a doorknob manipulandum and a key-grip manipulandum.

9. The apparatus of claim 8, wherein, the apparatus further comprises a platform connected for movement with the third joint such that the platform is generally horizontal in the equilibrium rest position, and the rotatable shaft is connected to be generally perpendicular to the platform in the equilibrium rest position, and wherein, if present:

the vertically split cylinder manipulandum comprises two cylinder halves which are spring biased apart and which are mounted on the rotatable shaft such that the user may squeeze, rotate on the rotatable shaft, or move the cylinder in the rotational degrees of freedom of the arm;

the doorknob manipulandum comprises a rotatable doorknob attached to the platform such that the user may rotate the doorknob relative to the platform, and may move the doorknob in the rotational degrees of freedom of the arm;

the key-grip manipulandum comprises a key way formed in the doorknob and a key tab fixed or tethered in the key way such that the user may rotate the key tab in the doorknob, pull the key tab in the key way, or move the doorknob in the rotational degrees of freedom of the arm;

the horizontal handles manipulandum comprises one or more handle mounted for rotation on an axle connected to the rotatable shaft in a manner such that the handles are generally horizontal in the equilibrium rest position, such that the user may rotate the handles on the axle, move the handles in a twisting motion along the long axis of the rotatable shaft, and move the handles in the rotational degrees of freedom of the arm;

the peg manipulandum comprises a peg which is spring biased in a housing connected to the platform such that the user may pull the peg against the spring and move the peg in the rotational degrees of freedom of the arm; and the coin manipulandum comprises a coin tethered to the platform such that the user may pick up the coin from the platform.

10. The apparatus of claim 9, further comprising one or more sensors located in one or more positions selected from the first, second and third joints, the first and second segments, and one or more of the manipulanda, the sensors being operative to detect movement or force and to generate an electrical signal representative of movement or force.

11. The apparatus of claim 10, further comprising locking means for locking one or more of the first joint, the second joint, the third joint, the rotatable shaft and the handle axle.

12. The apparatus of claim 6, further comprising one or more sensors located in one or more positions selected from the first, second and third joints, the first and second segments, and one or more of the manipulanda, the sensors being operative to detect movement or force and to generate an electrical signal representative of movement or force.

13. The apparatus of claim 12, further comprising a processing device for processing the electrical signal representative of movement or force, and means for transmitting the electrical signal to the processing device.

14. The apparatus of claim 13, wherein the one or more sensors are selected from potentiometers, gyroscopes, accelerometers, linear variable displacement transducers, optical encoders, strain gauges, electrical contacts, and photo-electric sensors.

15. The apparatus of claim 14, further comprising an electrical stimulator for activating nerves and muscles of the user to assist in manipulating the plurality of manipulanda.

16. The apparatus of claim 14, wherein the first and second segments are formed of a rigid material.

17. The apparatus of claim 14, wherein the processing device processes the electrical signal to generate feedback.

18. The apparatus of claim 17, wherein the processing device generates feedback in the form of an interactive computer game.

19. The apparatus of claim 14, wherein the processing device processes the electrical signal to generate performance ratings to evaluate a treatment or an exercise schedule.

20. The apparatus of claim 14, further comprising a telecommunications link between a computer located at the user's site and a remote computer under the control of a therapist.

21. The apparatus of claim 14, wherein the processing device includes software to prompt the user to manipulate the plurality of manipulanda through a series of movements from a standardized performance test.

22. The apparatus of claim 14, further comprising a horizontal support adjacent to the user, and one or more stationary manipulanda on the horizontal support within the reach of the user.

23. The apparatus of claim 22, wherein the stationary manipulanda includes a pegboard defining one or more holes and at least one peg tethered from a gantry positioned on the pegboard.

24. A method for providing an exercising therapy for a user's upper extremity, the method comprising the steps of:
providing the apparatus of claim 1; and
causing the user to manipulate the plurality of manipulanda with the user's hand to simulate movements representative of activities of the user's daily life.

25. The method of claim 24, wherein manipulating includes one or more of grasping, squeezing, releasing, pinching, lifting, lowering, moving from side to side, twisting and rotating.

26. The method of claim 24, further comprising:
providing one or more movement or force detecting sensors positioned in one or more locations selected from the arm, the plurality of joints or one or more of the manipulanda;
detecting with the one or more sensors, movement or force of any of the arm, the joints or the manipulanda;
generating an electrical signal from the detected movement or force; and
transmitting the electrical signal to a processing device to monitor the user's progress.

27. The method as set forth in claim 26, wherein the plurality of manipulanda is fixed or tethered to the free end of the arm such that the manipulanda so connected remain accessible to the user without dropping or becoming lost.

28. The method as set forth in claim 27, wherein one or more of the manipulanda are attached to the free end of the arm such that an additional rotational degree of freedom is provided to the manipulanda so attached.

29. The method as set forth in claim 28, wherein one or more of the manipulanda are mounted on a rotatable shaft connected at the free end of the arm such that the additional rotational degree of freedom is provided along the long axis of the shaft.

30. The method as set forth in claim 29, wherein the plurality of joints provides passive resistance against rotational movement, such that the arm and the manipulandum assembly adopt an equilibrium rest position when not in use.

31. The method of claim 30, wherein the arm is positioned above a floor, and wherein the arm is formed in two interconnected segments with a first segment extending generally upwardly from the base and a second segment extending generally forwardly toward the user to position the free end proximate the user's upper extremities, the first segment having the fixed end connected to the base through a first joint providing a rotational degree of freedom in a horizontal axis generally parallel to the floor, and a rotational degree of freedom in a vertical axis, the first and second segments being interconnected through a second joint providing a rotational degree of freedom in a horizontal axis, and the free end of the second segment being attached to the plurality of manipulanda through a third joint providing a rotational degree of freedom in a horizontal axis.

32. The method of claim 31, wherein the first, second and third joints are spring-loaded joints with a spring in the joint or ball and socket joints.

33. The method of claim 32, wherein at least one manipulanda is a vertically split cylinder manipulandum.

34. The method of claim 33, wherein, the apparatus further comprises a platform connected for movement with the third joint such that the platform is generally horizontal in the equilibrium rest position, and the rotatable shaft is connected to be generally perpendicular to the platform in the equilibrium rest position, and wherein, if present:

the vertically split cylinder manipulandum comprises two cylinder halves which are spring biased apart and which are mounted on the rotatable shaft such that the user may squeeze, rotate on the rotatable shaft, or move the cylinder in the rotational degrees of freedom of the arm;

the doorknob manipulandum comprises a rotatable doorknob attached to the platform such that the user may rotate the doorknob relative to the platform, and may move the doorknob in the rotational degrees of freedom of the arm;

the key-grip manipulandum comprises a key way formed in the doorknob and a key tab fixed or tethered in the key way such that the user may rotate the key tab in the doorknob, pull the key tab in the key way, or move the doorknob in the rotational degrees of freedom of the arm;

the horizontal handles manipulandum comprises one or more handle mounted for rotation on an axle connected to the rotatable shaft in a manner such that the handles are generally horizontal in the equilibrium rest position, such that the user may rotate the handles on the axle, move the handles in a twisting motion along the long axis of the rotatable shaft, and move the handles in the rotational degrees of freedom of the arm;

the peg manipulandum comprises a peg which is spring biased in a housing connected to the platform such that the user may pull the peg against the spring and move the peg in the rotational degrees of freedom of the arm; and the coin manipulandum comprises a coin tethered to the platform such that the user may pick up the coin from the platform.

35. The method of claim 34, further comprising one or more sensors located in one or more positions selected from the first, second and third joints, the first and second segments, and one or more of the manipulanda, the sensors being operative to detect movement or force and to generate an electrical signal representative of movement or force.

36. The method of claim 35, further comprising locking means for locking one or more of the first joint, the second joint, the third joint, the rotatable shaft and the handle axle.

37. The method of claim 31, further comprising one or more sensors located in one or more positions selected from the first, second and third joints, the first and second segments, and one or more of the manipulanda, the sensors being operative to detect movement or force and to generate an electrical signal representative of movement or force.

38. The method of claim 37, further comprising a processing device for processing the electrical signal representative of movement or force, and means for transmitting the electrical signal to the processing device.

39. The method of claim 38, wherein the one or more sensors are selected from potentiometers, gyroscopes, accelerometers, linear variable displacement transducers, optical encoders, strain gauges, electrical contacts, and photo-electric sensors.

40. The method of claim 39, further comprising an electrical stimulator for activating nerves and muscles of the user to assist in manipulating the plurality of manipulanda.

41. The method of claim 39, wherein the first and second segments are formed of a rigid material.

42. The method of claim 41, wherein the electrical signal is processed to generate feedback.

43. The method of claim 41, wherein the electrical signal is processed to generate feedback in the form of an interactive computer game.

44. The method of claim 41, wherein the electrical signal is processed to generate performance ratings to evaluate a treatment or an exercise schedule.

45. The method of claim 41, further providing a telecommunications link between a computer located at the user's site and a remote computer under the control of a therapist.

46. The method of claim 41, further comprising prompting the user to manipulate the plurality of manipulanda through a series of movements from a standardized performance test.

47. The method of claim 41, further comprising:
providing a horizontal support adjacent to the user; and
providing one or more stationary manipulanda on the horizontal support within the reach of the user.

48. The method of claim 47, wherein the stationary manipulanda includes a pegboard defining one or more holes and at least one peg tethered from a gantry positioned on the pegboard, and wherein the user is caused to move the peg into the one or more holes.

49. The method of claim 39, wherein the first and second segments are telescopic, elastic or rotational segments.

* * * * *